United States Patent [19]
Sarr et al.

[11] Patent Number: 4,766,554
[45] Date of Patent: Aug. 23, 1988

[54] ULTRASONIC INSPECTION SYSTEM WITH LINEAR TRANSDUCER ARRAY

[75] Inventors: Dennis P. Sarr, Kent; Fred D. Young, Bellevue, both of Wash.

[73] Assignee: The Boeing Company, Del.

[21] Appl. No.: 815,047

[22] Filed: Dec. 31, 1985

[51] Int. Cl.$^4$ .............................................. G01N 29/04
[52] U.S. Cl. ................................ 364/507; 364/571; 73/625; 73/628; 73/611
[58] Field of Search ............... 364/571, 550, 552, 507; 73/622, 625, 626, 628, 633, 644, 611

[56] References Cited

U.S. PATENT DOCUMENTS

| | | | |
|---|---|---|---|
| 3,575,043 | 4/1971 | Allen et al. | 73/67.8 |
| 3,857,052 | 12/1974 | Beller | 340/149 R |
| 3,911,730 | 10/1975 | Niklas | 73/67.7 |
| 4,070,905 | 1/1978 | Kossoff | 73/614 |
| 4,138,248 | 2/1979 | Narain | 75/101 R |
| 4,145,680 | 3/1979 | Smith | 340/5 MP |
| 4,170,142 | 10/1979 | Posakony et al. | 73/603 |
| 4,183,249 | 1/1980 | Anderson | 73/626 |
| 4,208,916 | 6/1980 | Thomenius et al. | 73/626 |
| 4,213,183 | 7/1980 | Barron et al. | 364/507 |
| 4,241,608 | 12/1980 | Dees et al. | 73/606 |
| 4,253,338 | 3/1981 | Iinuma et al. | 73/626 |
| 4,368,643 | 1/1983 | Tachita et al. | 73/626 |
| 4,387,597 | 6/1983 | Brandestini | 73/626 |
| 4,417,475 | 11/1983 | Okazaki | 73/626 |
| 4,446,715 | 5/1984 | Bailey | 364/571 |
| 4,462,082 | 7/1984 | Thiele et al. | 364/507 |

Primary Examiner—Parshotam S. Lall
Assistant Examiner—V. N. Trans
Attorney, Agent, or Firm—Finnegan, Henderson, Farabow, Garrett & Dunner

[57] ABSTRACT

Ultrasonic inspection apparatus includes a linear array of transmitting transducers and a linear array of receiving transducers providing TTU mode ultrasonic inspection. One to four transmitting transducers may be simultaneously pulsed as a group, and one to four receiving transducers may be simultaneously connected in common in a group by operation of a connection circuit. The connection circuit includes a plurality of multiplexor circuits having their signal inputs connected in common to respective receiving transducers and their address terminals connected to the data output terminals of programmable read only memory devices. Calibration means are provided for correcting the output signals produced by the receiving transducers to compensate for variations in the response of individual transducers.

15 Claims, 11 Drawing Sheets

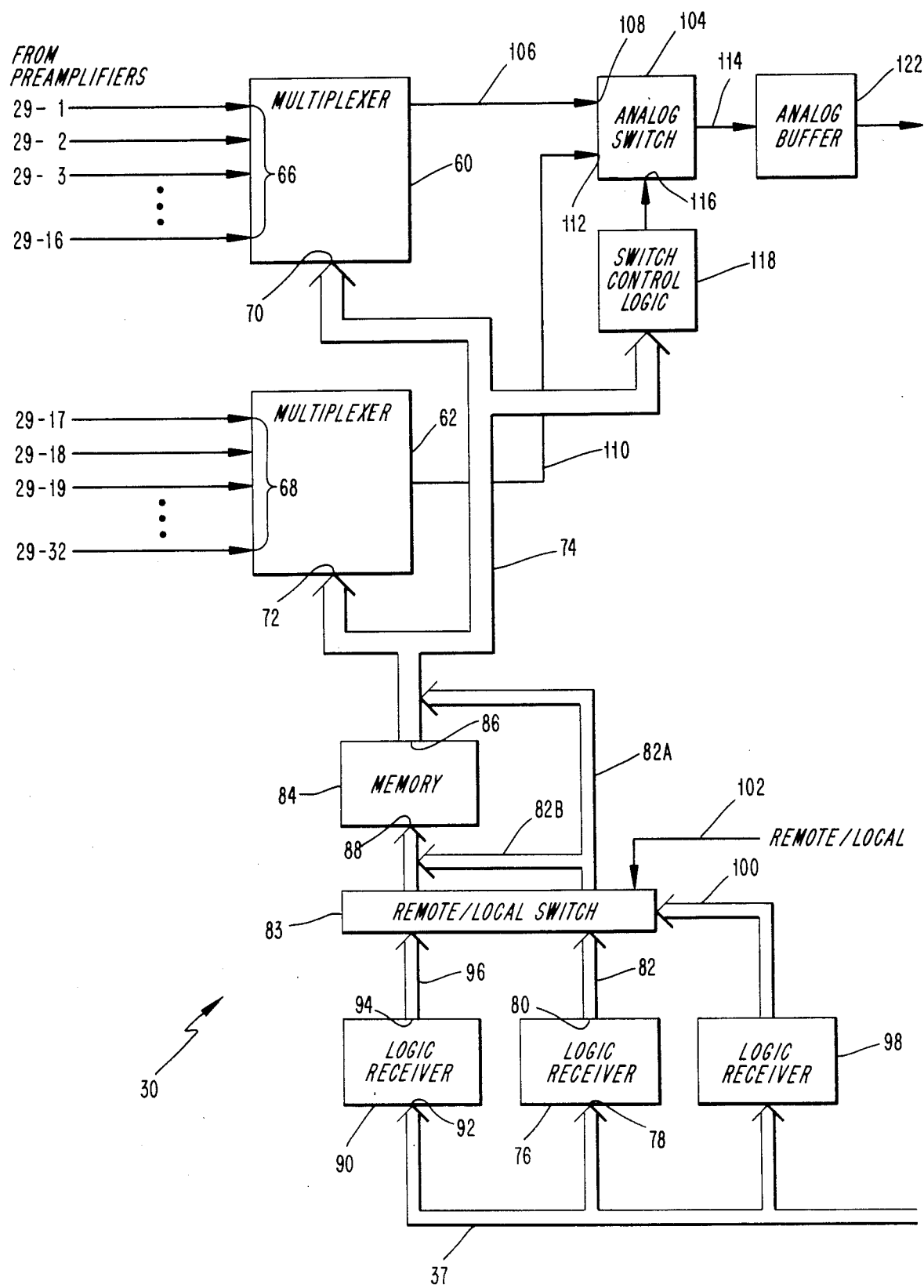

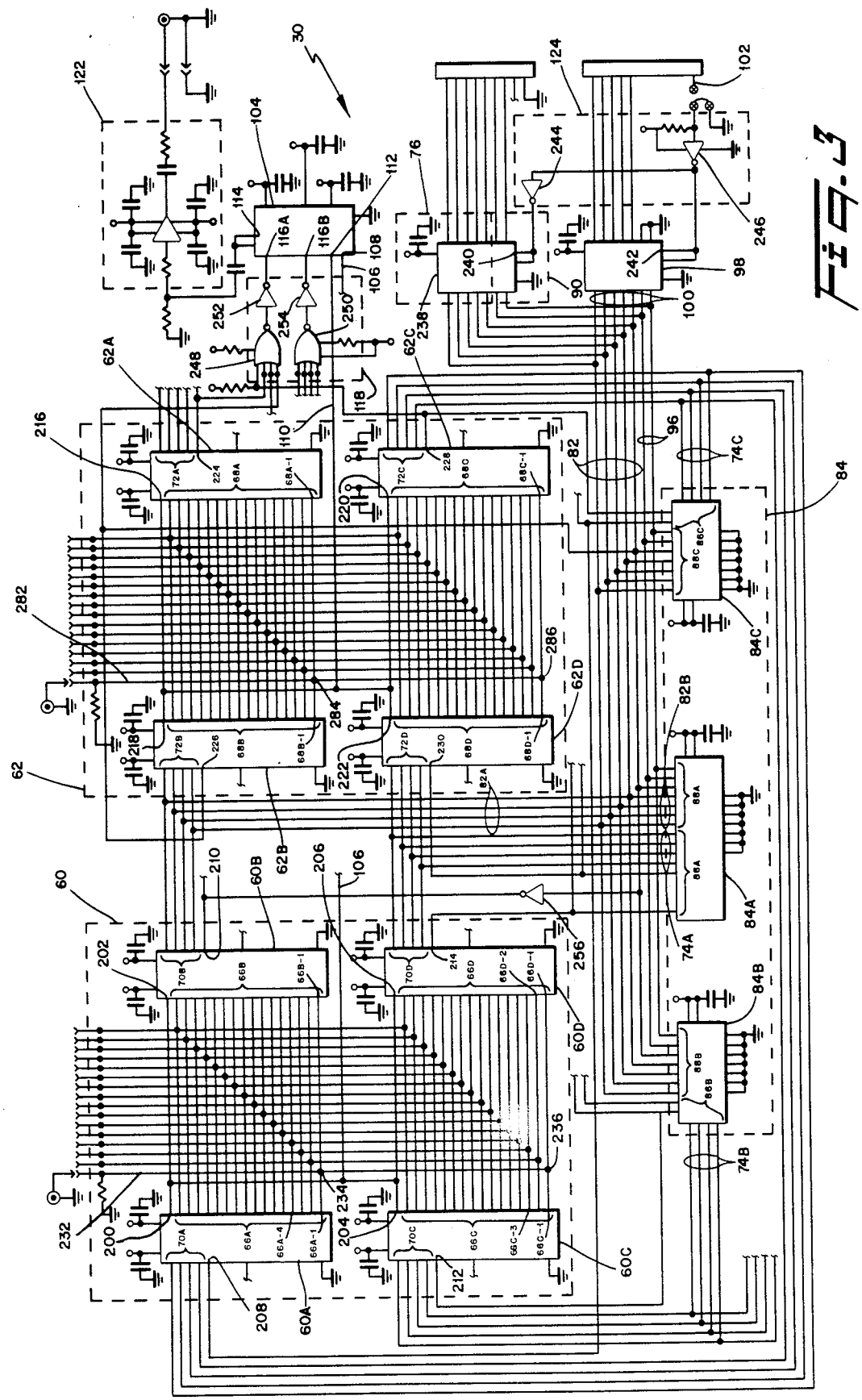

Fig. 4A

|  |  | 300 |  | 302 |  | 304 |  | 306 |
|---|---|---|---|---|---|---|---|---|
| ADDRESS | DATA | A | D | A | D | A | D | |
| 0 | 0 | 20 | 11 | 40 | 11 | 60 | 11 | |
| 1 | 0 | 21 | 12 | 41 | 12 | 61 | 12 | |
| 2 | 0 | 22 | 13 | 42 | 13 | 62 | 13 | |
| 3 | 0 | 23 | 14 | 43 | 14 | 63 | 14 | |
| 4 | 0 | 24 | 15 | 44 | 15 | 64 | 15 | |
| 5 | 0 | 25 | 16 | 45 | 16 | 65 | 16 | |
| 6 | 0 | 26 | 17 | 46 | 17 | 66 | 17 | |
| 7 | 0 | 27 | 18 | 47 | 18 | 67 | 18 | |
| 8 | 0 | 28 | 19 | 48 | 19 | 68 | 19 | |
| 9 | 0 | 29 | 1A | 49 | 1A | 69 | 1A | |
| A | 0 | 2A | 1B | 4A | 1B | 6A | 1B | |
| B | 0 | 2B | 1C | 4B | 1C | 6B | 1C | |
| C | 0 | 2C | 1D | 4C | 1D | 6C | 1D | |
| D | 0 | 2D | 1E | 4D | 1E | 6D | 1E | |
| E | 0 | 2E | 1F | 4E | 1F | 6E | 1F | |
| F | 0 | 2F | 20 | 4F | 20 | 6F | 20 | |
| 10 | 0 | 30 | 21 | 50 | 21 | 70 | 21 | |
| 11 | 0 | 31 | 22 | 51 | 22 | 71 | 22 | |
| 12 | 0 | 32 | 23 | 52 | 23 | 72 | 23 | |
| 13 | 0 | 33 | 24 | 53 | 24 | 73 | 24 | |
| 14 | 0 | 34 | 25 | 54 | 25 | 74 | 25 | |
| 15 | 0 | 35 | 26 | 55 | 26 | 75 | 26 | |
| 16 | 0 | 36 | 27 | 56 | 27 | 76 | 27 | |
| 17 | 0 | 37 | 28 | 57 | 28 | 77 | 28 | |
| 18 | 0 | 38 | 29 | 58 | 29 | 78 | 29 | |
| 19 | 0 | 39 | 2A | 59 | 2A | 79 | 2A | |
| 1A | 0 | 3A | 2B | 5A | 2B | 7A | 2B | |
| 1B | 0 | 3B | 2C | 5B | 2C | 7B | 2C | |
| 1C | 0 | 3C | 2D | 5C | 2D | 7C | 2D | |
| 1D | 0 | 3D | 2E | 5D | 2E | 7D | 2E | |
| 1E | 0 | 3E | 2F | 5E | 2F | 7E | 2F | |
| 1F | 0 | 3F | 0 | 5F | 0 | 7F | 0 | |
| | | | | | | 80 | 0 | |
| | | | | | | ↓ | ↓ | |
| | | | | | | FFF | 0 | |

Fig. 4-B

| ADDRESS | DATA | A (310) | D | A (312) | D | A (314) | D (316) |
|---|---|---|---|---|---|---|---|
| 0 | 0 | 20 | 0 | 40 | 12 | 60 | 12 |
| 1 | 0 | 21 | 0 | 41 | 13 | 61 | 13 |
| 2 | 0 | 22 | 0 | 42 | 14 | 62 | 14 |
| 3 | 0 | 23 | 0 | 43 | 15 | 63 | 15 |
| 4 | 0 | 24 | 0 | 44 | 16 | 64 | 16 |
| 5 | 0 | 25 | 0 | 45 | 17 | 65 | 17 |
| 6 | 0 | 26 | 0 | 46 | 18 | 66 | 18 |
| 7 | 0 | 27 | 0 | 47 | 19 | 67 | 19 |
| 8 | 0 | 28 | 0 | 48 | 1A | 68 | 1A |
| 9 | 0 | 29 | 0 | 49 | 1B | 69 | 1B |
| A | 0 | 2A | 0 | 4A | 1C | 6A | 1C |
| B | 0 | 2B | 0 | 4B | 1D | 6B | 1D |
| C | 0 | 2C | 0 | 4C | 1E | 6C | 1E |
| D | 0 | 2D | 0 | 4D | 1F | 6D | 1F |
| E | 0 | 2E | 0 | 4E | 20 | 6E | 20 |
| F | 0 | 2F | 0 | 4F | 21 | 6F | 21 |
| 10 | 0 | 30 | 0 | 50 | 22 | 70 | 22 |
| 11 | 0 | 31 | 0 | 51 | 23 | 71 | 23 |
| 12 | 0 | 32 | 0 | 52 | 24 | 72 | 24 |
| 13 | 0 | 33 | 0 | 53 | 25 | 73 | 25 |
| 14 | 0 | 34 | 0 | 54 | 26 | 74 | 26 |
| 15 | 0 | 35 | 0 | 55 | 27 | 75 | 27 |
| 16 | 0 | 36 | 0 | 56 | 28 | 76 | 28 |
| 17 | 0 | 37 | 0 | 57 | 29 | 77 | 29 |
| 18 | 0 | 38 | 0 | 58 | 2A | 78 | 2A |
| 19 | 0 | 39 | 0 | 59 | 2B | 79 | 2B |
| 1A | 0 | 3A | 0 | 5A | 2C | 7A | 2C |
| 1B | 0 | 3B | 0 | 5B | 2D | 7B | 2D |
| 1C | 0 | 3C | 0 | 5C | 2E | 7C | 2E |
| 1D | 0 | 3D | 0 | 5D | 2F | 7D | 2F |
| 1E | 0 | 3E | 0 | 5E | 0 | 7E | 0 |
| 1F | 0 | 3F | 0 | 5F | 0 | 7F | 0 |
|  |  |  |  |  |  | 80 ↓ FFF | 0 ↓ 0 |

Fig. 4-C

| ADDRESS | DATA | A (320) | D | A (322) | D | A (324) | D (326) |
|---|---|---|---|---|---|---|---|
| 0 | 0 | 20 | 0 | 40 | 0 | 60 | 13 |
| 1 | 0 | 21 | 0 | 41 | 0 | 61 | 14 |
| 2 | 0 | 22 | 0 | 42 | 0 | 62 | 15 |
| 3 | 0 | 23 | 0 | 43 | 0 | 63 | 16 |
| 4 | 0 | 24 | 0 | 44 | 0 | 64 | 17 |
| 5 | 0 | 25 | 0 | 45 | 0 | 65 | 18 |
| 6 | 0 | 26 | 0 | 46 | 0 | 66 | 19 |
| 7 | 0 | 27 | 0 | 47 | 0 | 67 | 1A |
| 8 | 0 | 28 | 0 | 48 | 0 | 68 | 1B |
| 9 | 0 | 29 | 0 | 49 | 0 | 69 | 1C |
| A | 0 | 2A | 0 | 4A | 0 | 6A | 1D |
| B | 0 | 2B | 0 | 4B | 0 | 6B | 1E |
| C | 0 | 2C | 0 | 4C | 0 | 6C | 1F |
| D | 0 | 2D | 0 | 4D | 0 | 6D | 20 |
| E | 0 | 2E | 0 | 4E | 0 | 6E | 21 |
| F | 0 | 2F | 0 | 4F | 0 | 6F | 22 |
| 10 | 0 | 30 | 0 | 50 | 0 | 70 | 23 |
| 11 | 0 | 31 | 0 | 51 | 0 | 71 | 24 |
| 12 | 0 | 32 | 0 | 52 | 0 | 72 | 25 |
| 13 | 0 | 33 | 0 | 53 | 0 | 73 | 26 |
| 14 | 0 | 34 | 0 | 54 | 0 | 74 | 27 |
| 15 | 0 | 35 | 0 | 55 | 0 | 75 | 28 |
| 16 | 0 | 36 | 0 | 56 | 0 | 76 | 29 |
| 17 | 0 | 37 | 0 | 57 | 0 | 77 | 2A |
| 18 | 0 | 38 | 0 | 58 | 0 | 78 | 2B |
| 19 | 0 | 39 | 0 | 59 | 0 | 79 | 2C |
| 1A | 0 | 3A | 0 | 5A | 0 | 7A | 2D |
| 1B | 0 | 3B | 0 | 5B | 0 | 7B | 2E |
| 1C | 0 | 3C | 0 | 5C | 0 | 7C | 2F |
| 1D | 0 | 3D | 0 | 5D | 0 | 7D | 0 |
| 1E | 0 | 3E | 0 | 5E | 0 | 7E | 0 |
| 1F | 0 | 3F | 0 | 5F | 0 | 7F | 0 |
| | | | | | | 80 ↓ FFF | 0 ↓ 0 |

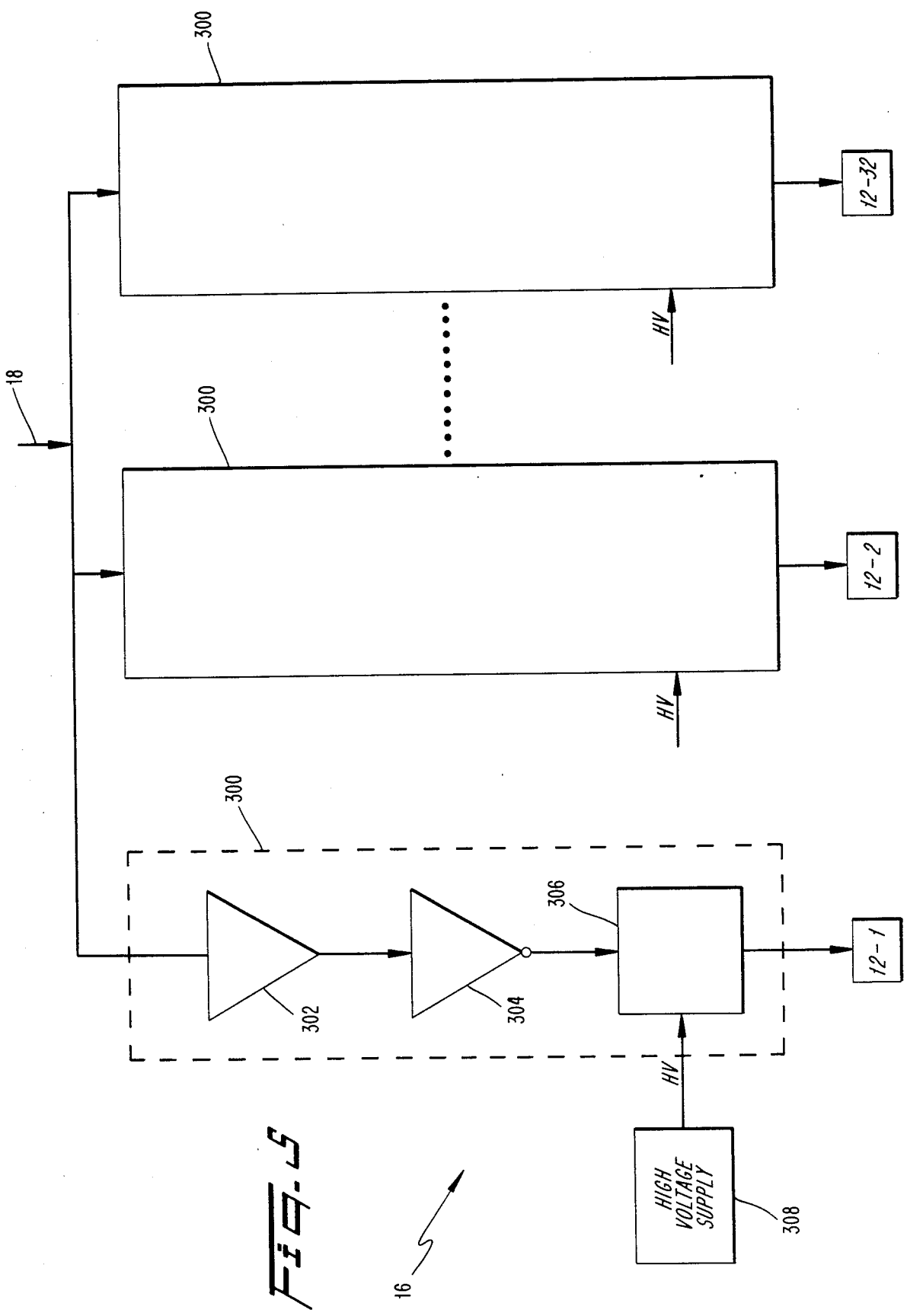

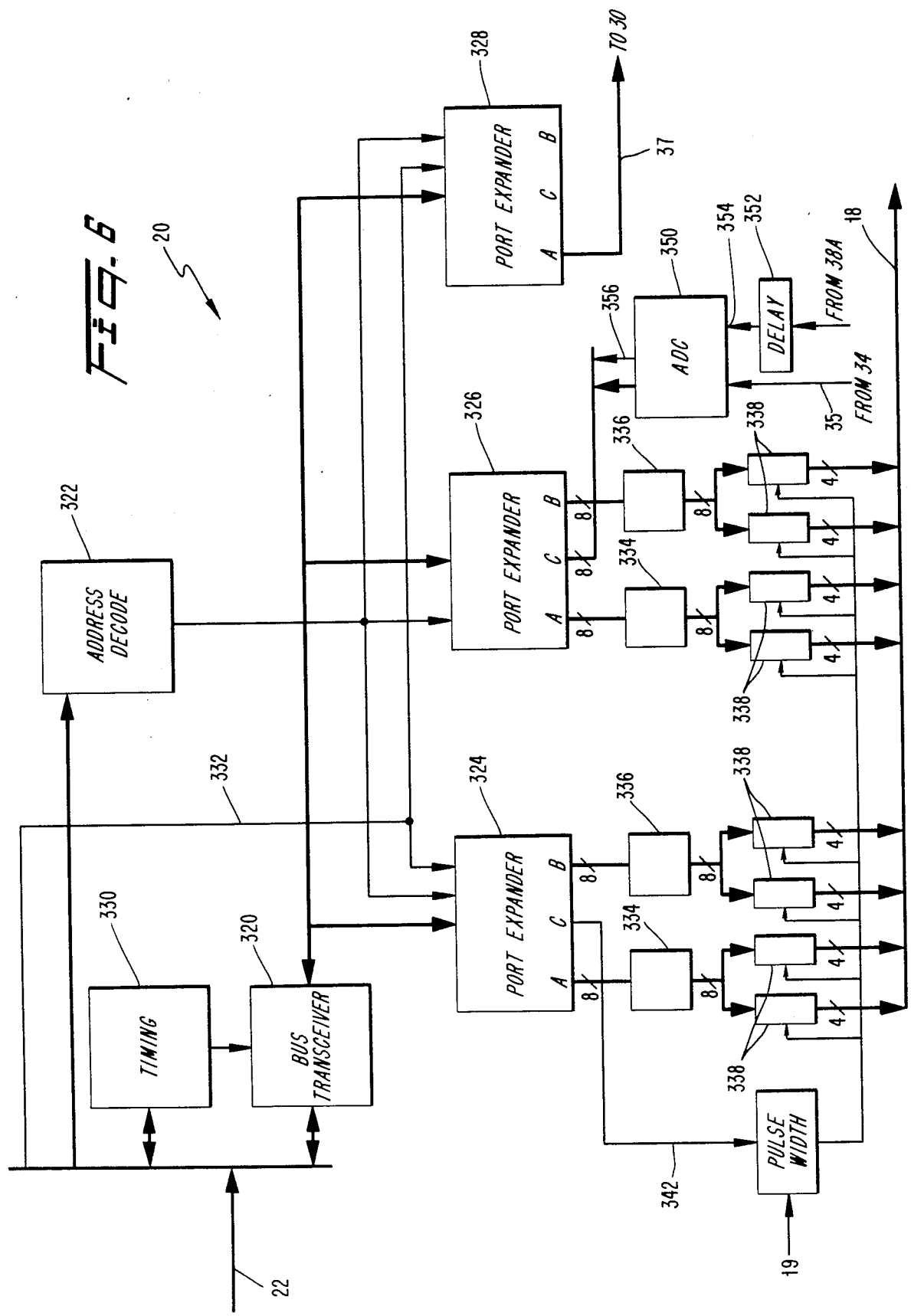

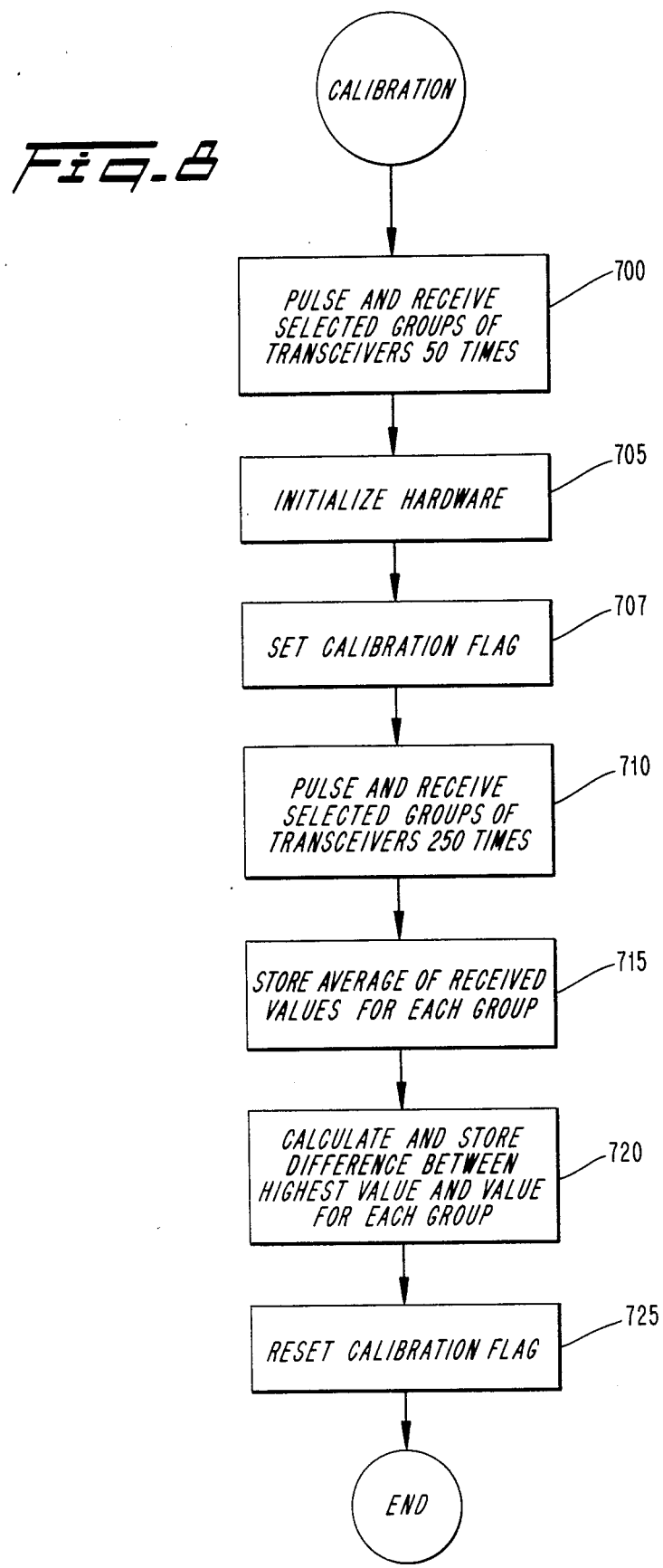

ULTRASONIC INSPECTION SYSTEM WITH LINEAR TRANSDUCER ARRAY

CROSS REFERENCE TO RELATED APPLICATIONS

The invention is related to the following copending U.S. patent applications assigned to the assignee of the present invention:
DATA RECORDING APPARATUS FOR AN ULTRASONIC INSPECTION SYSTEM, Ser. No. 06/815,050, filed on Dec. 31, 1985 by D. P. Sarr, allowed;
ULTRASONIC INSPECTION SYSTEM APPARATUS AND METHOD FOR RECEIVING MULTIPLE TRANSDUCER ELEMENTS, Ser. No. 06/815,048, filed on Dec. 31, 1985, by D. P. Sarr, allowed;
ULTRASONIC INSTRUMENTATION FOR EXAMINATION OF VARIABLE-THICKNESS OBJECTS, Ser. No. 06/815,038, filed on Dec. 31, 1985 by D. P. Sarr, allowed;
AN IMPROVED ULTRASONIC TESTING APPARATUS, Ser. No. 06/815,163, filed Dec. 31, 1985 by G. A. Geithman and D. P. Sarr, allowed;
ULTRASONIC TRANSDUCER WITH SHAPED BEAM INTENSITY PROFILE, Ser. No. 06/815,162, filed Dec. 31, 1985 by G. A. Geithman and D. H. Gilbert, now U.S. Pat. No. 4,700,575; and
ULTRASONIC 64 CHANNEL INSPECTION SYSTEM WITH MULTIGATE/MULTI MODE SELECTION, SOFTWARE CONFIGURABILITY, Ser. No. 06,815,044, filed Dec. 31, 1985 by D. P. Sarr.
The disclosures of these applications are hereby incorporated by reference.

BACKGROUND OF THE INVENTION

The invention relates to ultrasonic inspection and, more particularly, to apparatus and methods for simultaneously generating inspection pulses from a plurality of ultrasonic transmitting transducers and simultaneously receiving data from a plurality of ultrasonic receiving transducers.

Ultrasonic inspection is widely used in the marufacture of components for aircraft and other industrial equipment. In many applications, every portion of a part must be examined Therefore, ultrasonic inspection systems typically employ a large number of transducers in order to keep the inspection time per unit at an acceptable value. Unlike ultrasonic imaging systems employed in the medical field, ultrasonic defect detection systems are not concerned with providing a cross-sectional image of an organ or component being inspected, but rather to determine the presence or absence of structural defects in such components. For certain types of components, arrays of transducers are employed in a mode known as Through Transmission Ultrasonic (TTU) inspection in which a first array of transducers is disposed on one side of a work piece to transmit ultrasonic energy and a second array of ultrasonic transducers is disposed on the opposite side of the workpiece to receive the ultrasonic energy transmitted through the workpiece.

For materials exhibiting a high ultrasonic attenuation, such as honeycomb material, it is necessary to apply large amounts of ultrasonic energy to the workpiece in order to obtain the required signal-to-noise ratio at the receiving end. One method of providing such large amounts of transmitted ultrasonic energy is to simultaneously energize two or more ultrasonic transmitting transducers. Data from a corresponding number of receiving transducers may be simultaneously received and analyzed to detect the presence of defects. For example, for certain types of honeycomb material, it has been determined that the simultaneous energization of four ultrasonic transducers can provide the requisite amount of energy input to the workpiece. Other types of workpieces may be most advantageously inspected using the simultaneous energization of other numbers of transmitting transducers, for example, two or three.

In such situations, it is usually desirable to simultaneously receive data from a corresponding number of receiving transducers. For other applications, however, it has been determined that defects may be more readily detected when data is analyzed by simultaneously receiving from a differing number of receiving transducers. However, in prior art ultrasonic defect detection systems, it was difficult or impossible to readily change the number of ultrasonic receiving transducers from which data was simultaneously received independently of the number of simultaneously energized transmitting transducers.

It is therefore an object of the present invention to provide an apparatus and methods for ultrasonic detection of defects having greater flexibility in establishing simultaneous energization of transmitting tranducers and simultareous reception from a plurality of receiving transducers. It is a further object of the invention to provide such apparatus and methods at the lowest possible cost.

SUMMARY OF THE INVENTION

The present invention overcomes the problems of the prior art and achieves the objects listed above by providing apparatus for simultaneously energizing a plurality of transmitting transducers and for simultaneously receiving from a plurality of receiving transducers independent of the transmitting transducers.

In particular, to achieve the objects and in accordance with the purpose of the invention, as embodied and as broadly described in the specification, an ultrasonic inspection system is provided which comprises a plurality of ultrasonic transmitting transducers; means for energizing selectable groups of the transmitting transducers; a plurality of ultrasonic receiving transducers, each of the receiving transducers generating a data output signal representative of ultrasonic energy received by the receiving transducer; means for combining the data output signals of selectable groups of the receiving transducers independent of the transmitting transducer groups and for supplying a second output signal representive of the combined data output signals, and calbration means for correcting the data output signals of the receiving transducers to compensate for individual variation in the response of the receiving transducers.

In another aspect, the invention provides a method for generating ultrasonic inspection data from an array of ultrasonic transmitting transducers and an array of ultrasonic receiving transducers which generate data output signals representative of received ultrasonic energy. The method comprises the steps of energizing the array of ultrasonic transmitting transducers by generating sequential inspection pulses each consisting of simultaneously energized selectable groups of the transmitting transducers; and generating sequential output data values by combining the data output signals of sequentially selected groups of the receiving transducers independent of the transmitting transducer groups.

BRIEF DESCRIPTION OF THE DRAWINGS

FIG. 2 is a block diagram of the common connection circuit shown in FIG. 1;

FIG. 3 is a detailed schematic diagram of the common connection circuits shown in FIG. 2;

FIGS. 4A-4C show data values stored in memory devices of the common connection circuit shown in FIG. 2;

FIG. 5 is a detailed block diagram of the high voltage pulser circuit shown in FIG. 1;

FIG. 6 is a detailed block diagram of the pulser/receiver control circuit of FIG. 1;

FIG. 8 is a logic flow diagram of the calibration routine of FIG. 7.

DESCRIPTION OF THE PREFERRED EMBODIMENT

Figure 1:
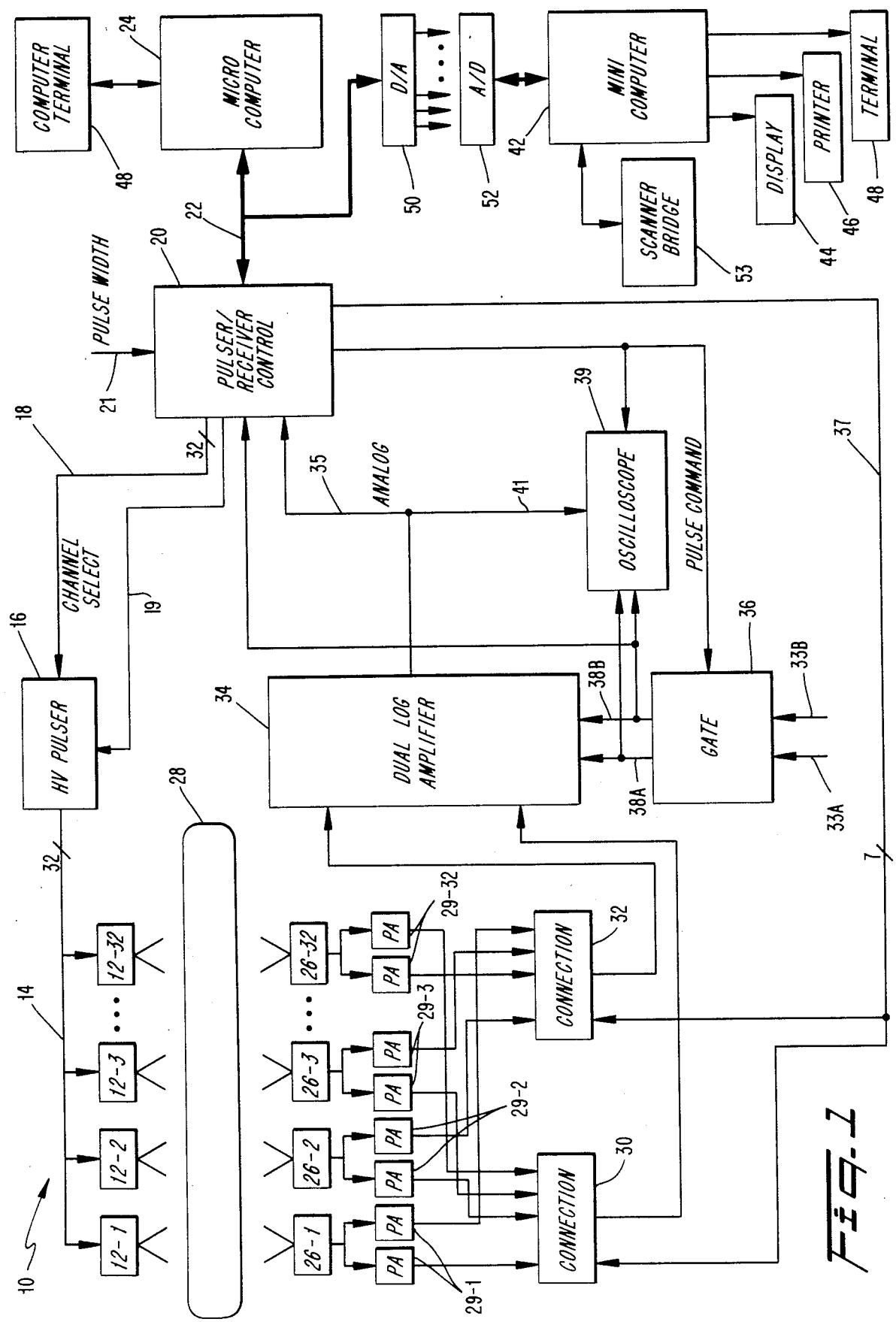
FIG. 1 is a block diagram of an ultrasonic inspection system which constitutes a preferred embodiment of the present invention.

Reference will now be made in detail to a presently preferred embodiment of this invention, an example of which is illustrated in the accompanying drawings in which like reference characters refer to corresponding elements.

FIG. 1 shows an ultrasonic inspection system 10 including a linear array of thirty two ultrasonic transmitting transducers 12-1 through 12-32. Throughout this description, ultrasonic transmitting transducers will be referred to both by the collective reference character 12 or by reference character 12-X where X is 1 to 32, where it is desired to refer to the entire array or to individual transducers, respectively.

The invention includes means for energizing transmitting transducers, and specifically for energizing selectable groups of adjacent transmitting transducers 12. As can be seen in FIG. 1, transducers 12 are connected by a thirty two line high-voltage bus 14 to a high voltage pulser circuit 16. Pulser circuit 16 is connected via a thirty two-bit bus 18 and control line 19 to a pulser/receiver control circuit 20. Pulser/receiver control circuit 20 is in turn connected over a multiple conductor bus 22 to a microcomputer 24. In the preferred embodiment, microcomputer 24 comprises an Intel System 80 Microcomputer System with an Intel SBC 86/30 interface board. Bus 22, in the preferred embodiment, comprises a bus established according to the Intel Multibus protocol.

As is shown in FIG. 1, a linear array of ultrasonic receiving transducers 26-1 through 26-32 is disposed on the opposite side of a workpiece 28 from transmitting transducers 12. Throughout this description, ultrasonic receiving transducers will be referred to both by the collective reference character 26 or by reference character 26-X where X is 1 to 32, where it is desired to refer to the entire array or to individual transducers, respectively. Receiving transducers 26 each generate a data output signal representative of ultrasonic energy received by the transducer.

The invention includes means for combining data output signals of selectable groups of receiving transducers 26 independent of the transmitting transducer groups and for supplying a second output signal representative of the combined data output signals. Specifically, the invention includes means for combining the data output signals of groups of adjacent receiving transducers 26. In the preferred embodiment as shown in FIG. 1, each of receiving transducers 26 is connected through respective pairs of preamplifiers 29-1 through 29-32 to first and second connection circuits 30, 32. Preamplifier pairs will be referred to either collectively by the reference character 29 or individually by 29-X where X is 1 to 32.

Outputs from connection circuits 30 and 32 are supplied to an amplifier 34. Control inputs to connection circuits 30 and 32 are provided by pulser/receiver control circuit 20 cover a bus 37.

In the preferred embodiment, amplifier 34 includes a dual logarithmic amplifier circuit similar to that described in greater detail in the aforementioned U.S. patent application Ser. No. 815,163. Amplifier 34 requires two identical inputs from connection circuits 30 and 32 and provides a single high-accuracy, wide dynamic range analog signal. A single input amplifier may also be used, in which case only a single connection circuit 30 would be required.

A gate circuit 36 is also connected to pulser/receiver control circuit 20 and generates control signals 38A, 33B for amplifier 34. Gate delay and gate length input signals to gate 36 are provided by operator entry as indicated at 33A, 33B. The output of amplifier 34 is supplied to pulser/receiver control circuit 20 over a line 35 and to an osilloscope 39 over a line 41. Control signals 38A and 38B constitute GATE ENABLE and SAMPLE READ signals, respectively, as described more completely in the aforementioned U.S. patent application Ser. No. 815,163. Gate 36 also supplies signals 38A, 38B to oscilloscope 39 for set-up purposes.

Microcomputer 24 is connected via bus 22 to a digital-to-analog converter (DAC) circuit 50, which provides thirty two channels of analog outputs representative of the amount of ultrasonic energy received by transducers 26. In the preferred embodiment, the outputs of DAC circuit 50 are supplied through an analog to digital converter (ADC) 52 to a display system based on a Data General Type MV4000 minicomputer 42. Minicomputer 42 is connected to a display device 44 and a printer 46. Other types of display systems could also be used, such as a strip chart recorder.

A scanner bridge 53 is connected to minicomputer 42. Scanner bridge 53 supports transducer 12 and 26 and is moved across workpiece 28, under control of minicomputer 42 to ultrasonically inspect workpiece 28.

Also connected to microcomputer 24 is a computer terminal 48, which in the preferred embodiment comprises an Ann Arbor K 2480 terminal. As will be more completely described hereinafter, operator inputs through control terminal 48 are received by microcomputer 24 to establish the number of transmitting transducers 12 which are desired to be simultaneously energized and the number of receiving transducers 26 from which data will be simultaneously received. Microcomputer 24 then generates control signals to pulser/receiver control circuit 20 to simultaneously energize selected ones of the thirty-two transducers 12-1 through 12-32. Control circuit 20 performs this energization by transmitting channel select signals at a TTL logic level over selected lines of bus 18 to voltage pulser circuit 16.

The pulse width of the channel select signals is specified by operator input at a terminal 21.

High voltage pulser circuit 16 receives the TTL level channel select signals corresponding to the selected transducers 12 and generates corresponding high voltage pulses over corresponding lines of bus 14 to energize the selected transducers 12. The selected transducers 12 then generate ultrasonic signals which are transmitted through workpiece 28 to the array of receiving transducers 26.

Microcomputer 24 also initiates selection signals through control circuit 20 over bus 37 to connection circuits 30 and 32. Connection circuit 30 then simultaneously connects the outputs of specified receiving transducers 26 to amplifier 34. The peak value of output signals from the selected transducers 26 is then sampled by amplifier 34 during a time window established by gate 36 and supplied as an analog signal over line 35 to control circuit 20. Control circuit 20 then converts the analog signals supplied over line 35 to a digital quantity for transmission to microcomputer 24. Microcomputer 24 then supplies the data via DAC circuit 50 and ADC 52 to minicomputer 42 in which the data is manipulated into appropriate format for output to display 44 and printer 46. Oscilloscope 39 also provides a display of data received by transducers 26.

Referring now to FIG. 2, connection circuit 30 is shown in greater detail. In accordance with the invention, first control means are provided for generating a first selection signal identifying a first associated receiving transducer. In the preferred embodiment, a logic receiver 76 shown in FIG. 2 provides these functions. Logic receiver 76 includes input terminals 78 connected to bus 37 from pulser/receiver control circuit 20. Logic receiver 76 also includes output terminals 80 connected over a bus 82 and a remote/local switch 83 to an address bus 74.

The invention further includes second control means for generating a multiple connection code specifying a number of associated receiving transducers for which output signals are to be combined with the output signal of the first associated receiving transducer. In the preferred embodiment, a logic receiver 90, also shown in FIG. 2, performs these functions. Logic receiver 90 includes input terminals 92 connected over bus 37 to pulser/receiver control circuit 20 and output terminals 94 connected to a bus 96.

In accordance with the invention there is also provided conversion means connected to the second control means for converting the multiple connection code to second selection signals identifying specific ones of the associated receiving transducers 26 other than the first associated transducer 26. In the preferred embodiment, a memory circuit 84 provides these functions. Memory circuit 84 includes data output terminals 86 connected to address bus 74. Memory circuit 84 also includes address input terminals 88.

The invention includes connection means for coupling the output of the first associated transducer to the outputs of specific other associated receiving transducers, the connection means connected to the first control means and the conversion means such that said first selection signal is supplied to the connection means independent of the conversion means. In the preferred embodiment, multiplexer circuits 60 and 62 provide these functions. Each of multiplexer circuits 60 and 62 comprises sixteen signal input terminals 66 and 68, respectively, and address input terminals 70 and 72, respectively. Input signals are supplied to multiplexer address input terminals 70 and 72 over address bus 74. Terminals 66 and 68 are connected to the outputs of one member of respective preamplifier pairs 29-1 through 29-32.

As can be seen in FIG. 2, a logic receiver 98 is also provided, having inputs connected to bus 37. The output of logic receiver 98 is supplied over a bus 100 to remote/local switch 83 operating under control of a remote/local switch line 102. Operation of remote/local switch line 102 is operable to isolate logic receivers 76 and 90 (supplied with signals from microcomputer 24) from the input to memory device 84 and address line 74, and provide as a substitute signals locally generated by pulser/receiver control circuit 20 for maintenance and debugging purposes.

In accordance with the present invention, there is provided switch means for selectively connecting the outputs of multiplexer circuits 60 and 62. Analog switch 104 performs these functions. The output of multiplexer circuit 60 is provided over a line 106 to one input 108 of analog switch 104. The output of multiplexer circuit 62 is connected over a line 110 to the other input 112 of analog switch 104. Inputs 108 and 112 are selectively connected to an output terminal 114 of analog switch 96 as specified by control signals supplied to a control terminal 116. That is, output 114 may be connected to either or both input terminals 108 or 112.

Control signals are supplied to terminal 116 by a switch control logic circuit 118, the input of which is connected over a bus 74 to memory data output terminals 86. Output terminal 114 of analog switch 104 is connected through an analog buffer 122 to amplifier circuit 34.

In order to simplify the description of system 10, only the operation of circuit 30 will now be described. However, it is to be understood that in the preferred embodiment circuit 32 operates simultaneously with circuit 30 and in an identical manner to generate an identical output signal to amplifier 34.

As specified by program instructions to be more completely described, microcomputer 24 (FIG. 2) provides signals over bus 37 to specify a first selected receiving transducer 26, the output of which is to be connected to amplifier 34, and to specify a number of adjacent receiving transducers 26, the outputs of which are to be combined with the output of the first selected receiving transducer 26 and connected to amplifier 34. Signals over bus 37 are received by logic receivers 76 and 90 which respectively generate a first selection signal and a multiple connection code. The first selection signal is supplied over a portion 82A of bus 82 and over address bus 74 to address input terminals 70, 72 of multiplexer circuit 60, 62, respectively. The multiple connection code is supplied by logic receiver 90 over bus 96 to address input terminals 88 of memory 84. Memory 84, in response to the multiple connection code, supplies a second selection signal from data stored in memory 84 over data output terminals 86 through address bus 74 to address input terminals 70, 72 of multiplexer circuits 60, 62. In response to these signals, multiplexer circuits 60, 62 connect the outputs of the specified receiving transducers 26 in common over output lines 106 and 110 to input terminals 108 and 112 of analog switch 104.

In the preferred embodiment, the outputs of transducers 26 may be combined in groups of one, two, three, or four and supplied to the input of amplifier 34. For example, it may be desired to simultaneously connect the outputs of four transducers to amplifier 34 and initiate a scan beginning with receiving transducer 26-1 and ending with receiving transducer 26-32. That is, receiving transducers 26-1, 26-2, 26-3, and 26-4 would first have their outputs connected simultaneously to amplifier 34 to receive ultrasonic energy generated by a pulse of one or more transmitting transducers 12-1 through 12-32. During the next pulse, receiving transducers 26-2, 26-3, 26-4, and 26-5 would be simultaneously connected. The third pulse would call for receiving transducers 26-3, 26-4, 26-5, and 26-7 to be simultaneously connected. In a similar manner, the entire array of transducers 26 would be scanned such that the twenty-ninth pulse scan would constitute simultaneous connection of the outputs of receiving transducers 26-29, 26-30, 26-31, and 26-32 to amplifier 34.

It can be appreciated that when microcomputer 24 calls for simultaneous connection of four transducers, such transducers may be associated with either or both multiplexer circuits 60 or 62. Thus, the outputs of circuits 60 and 62 must be connected either individually or in common to the output of circuit 30. Such connections are established by analog switch 104 through operation of switch control logic 118 in response to second selection signals generated at terminals 86 of memory 84, in a manner to be more completely described hereinafter.

Referring now to FIG. 3, the construction of connection circuit 30 is shown in greater detail. As can be seen therein, memory circuit 84 is formed from three programmable read-only memory (PROM) devices 84A, 84B, and 84C. In the preferred embodiment, PROMS 84A-84C comprise type I2716-1 integrated circuit PROMS commercially available from the Intel Corporation. PROMS 84A-84C each include eight address input terminals, seven of which are employed in the present invention. Thus, PROMS 84A, 84B, and 84C include memory address input terminals 88A, 88B, and 88C, respectively. PROM's 84A, 84B and 84C also each include eight data output terminals, six of which are utilized in the present invention. Thus, PROMS 84A, 84B, and 84C each include memory data output terminals 86A, 86B, and 86C, respectively.

In the preferred embodiment, analog switch 104 comprises a type IH5141CPE two-input analog switching integrated circuit obtainable in commercial quantities from the Intersil Corporation of Cupertino, Calif. Switch 104 includes a pair of control terminals 116A and 116B, and an output terminal 114 connected to analog buffer 122 which, in the preferred embodiment, comprises a type LH0002CH integrated circuit current amplifier obtainable in commercial quantities from the National Semiconductor Corporation of Santa Clara, Calif.

As can be seen in FIG. 3, switch control logic circuit 118 comprises a pair of four-input NOR gates 248 and 250, the outputs of which are connected through an inverter 252 to input terminal 116A and through an inverter 254 to input 116B, respectively, of analog switch 104.

Multiplexer circuit 60 includes four identical 16:1 multiplexer devices 60A, 60B, 60C, 60D. Multiplexer circuit 62 also includes four identical 16:1 multiplexer devices 62A, 62B, 62C, and 62D. Multiplexer devices 60A-60D and 62A-62D in the preferred embodiment each comprise type DG506A 16:1 multiplexer integrated circuits available in commercial quantities from the Siliconix Corporation of Santa Clara, Calif. Each of multiplexer devices 60A-60D includes a set of sixteen signal input terminals 66A-66D, respectively, a set of address input terminals 70A-70D respectively, an output terminal 200, 202, 204, and 206, respectively, and an enable terminal 208, 210, 212, and 214, respectively. Similarly, each of multiplexer devices 62A-62D includes a set of sixteen signal input terminals 68A-68D, a set of four address input terminals 72A-72D, an output terminal 216, 218, 220, and 222, and an enable terminal 224, 226, 228, and 230, respectively. Devices 60A-60D and 62A-62D are responsive to first and second selection signals supplied to address input terminals 70A-70D and 72A-72D to couple one of the the signal input terminals 66A-66D or 68A-68D to output terminals 200-206 or 224-230.

As can be seen in FIG. 3, output signals from one member of each of preamplifier pairs 29-1 through 29-16 of receiving transducers 26-1 through 26-16 is connected to a respective input terminal of each of multiplexer devices 60A-60D. For example, the output signal from preamplifier 29-1 connected to receiving transducer 26-1 is connected over a signal line 232 to a junction 234 which is commonly connected to signal input terminal 66A-1 of multiplexer device 60A and signal input terminal 66B-1 of multiplexer device 60B. Signal line 232 is also connected to a junction 236 which is commonly connected to signal input terminal 66C-1 of multiplexer device 60C and signal input terminal 66D-1 of multiplexer device 60D. In a similar manner, output signal lines from preamplifiers 29-2 through 29-16 associated with receiving transducers 26-2 through 26-16 are connected to respective signal input terminals of each of multiplexer devices 60A-60D.

Output terminals 200, 202, 204 and 206 of multiplexer devices 60A, 60B, 60C, and 60D, respectively, are connected in common to output signal line 106 which is connected to analog switch 104.

Enable terminals 208 of multiplexer device 60A are connected to data output terminals 86C of PROM 84C and to NOR gate 250. Enable terminal 210 of multiplexer device 60B is cornected to NOR gate 250 and through an inverter 256 to bus 96. Enable terminal 212 of multiplexer device 60C is connected to data output terminals 86B of PROM 84B and to NOR gate 250. Enable terminal 214 of multiplexer device 60D is connected to data output terminals 86A of PROM 84A and to NOR gate 250.

In a similar manner output signals from preamplifiers 29-17 through 29-32 of receiving transducers 26-17 through 26-32 are each connected to a respective input terminal of each of multiplexer devices 62A-62D. For example, the output signal from preamplifier 29-17 connected to receiving transducer 26-17 is connected over a signal line 282 to a junction 284 which is commonly connected to signal input terminal 68A-1 of multiplexer device 62A and signal input terminal 68B-1 of multiplexer device 62B. Signal line 282 is also connected to a junction 286 which is commonly connected to signal input terminal 68C-1 of multiplexer device 62C and signal input terminal 68D-1 of multiplexer device 62D. In a similar manner, output signal lines from preamplifiers 29-18 - 29-32 associated with receiving transducers 26-18 through 26-32 are connected to respective to signal input terminals each of multiplexer devices 62A-62D.

Output terminals 216, 218, 220, and 222 of multiplexer devices 62A, 62B, 62C, and 62D, respectively, are connected in common to output signal line 110 which is connected to analog switch 114.

Enable terminal 224 of multiplexer device 62A is connected to data output terminals 86B of PROM 84B and to NOR gate 298. Enable terminal 226 of multiplexer device 62B is connected to bus 82 and to NOR gate 248. Enable terminal 228 is connected to data output terminals 86C of PROM 84C and to NOR gate 248. Enable terminal 228 of multiplexer device 62D is connected to data output terminals 86A of PROM 84A, to to NOR gate 248.

As can be seen in FIG. 3, multiplexer address bus 74 comprises portion 74A, 74B, and 74C respectively connected to memory data output terminals 86A, 86B, and 86C.

Address terminals 70A of multiplexer device 60A and address terminals 72C of multiplexer device 62C are connected in common data output terminals of 86C of PROM 84C. Address terminals 70B of multiplexer device 60B and address terminals 72B of multiplexer device 62B are connected in common to Bus 82B. Address terminals 70C of multiplexer device 60C and address terminals 72A of multiplexer device 62A are connected in common to data output terminals 86B of PROM 84B. Address terminals 70D of multiplexer device 60D and address terminals 72D of multiplexer device 62D are connected in common to data output terminals of 86A of PROM 84A.

As can be seen in FIG. 3, the functions of logic receivers 76 and 90 of FIG. 2 are performed by a single integrated circuit logic receiver device 238. Logic receiver device 238 in the preferred embodiment comprises a type 74LS244N logic receiver integrated circuit obtainable in commercial quantities from Texas Instruments, Inc. Similarly, logic receiver 98 may comprise a type 74LS244 logic receiver integrated circuit. Logic receiver devices 238 and 98 each include respective enable terminals 240, 242 connected to the outputs of inverters 244 and 246, respectively. The input of inverter 244 is connected to the output of inverter 246. The input of inverter 246 is connected to local/remote signal line 102.

The output of logic receiver 98 is connected through bus 100 in common with the output of logic receiver 238 to form bus 96 and bus 82.

PROMs 84A, 84B, and 84C each include data stored therein as shown in FIGS. 4A, 4B, and 4C, respectively. Throughout the remainder of the description of the preferred embodiment, numbers expressed in hexidecimal notation will have an appended suffix H.

As can be seen in FIG. 4A, PROM 84A includes a first set of data 300 stored in addresses 0–1FH of PROM 84A consisting of a string of zeros. PROM 84A also includes data sets 302, 304, and 306 located in addresses 20–3FH, 40–5FH, and 60–7FH, respectively. No data is present in the remainder of PROM 84A located in addresses 80–FFFH.

FIG. 4B shows the data stored in PROM 84B. PROM 84B includes data sets 310, 312, 314, and 316 stored in addresses 0–1FH, 20–3FH, 40–5FH, and 60–7FH, respectively. The remainder of PROM 84B having addresses 80–FFFH has no data stored therein.

Referring to FIG. 4C, PROM 84C includes data sets 320, 322 324, and 326 stored in addresses 0–1FH, 20–3FH, 40–5FH and 60–7FH, respectively. The remainder of PROM 84C in addresses 80–FFFH has no data stored therein.

The operation of connection circuit 30 will now be described. Through information entered by an operator through computer terminal 48, microcomputer 24 sends commands over bus 22 through pulser/receiver control circuit 20 to connection circuit 30 to connect output signals from selected transducers 26-1 through 26-32 to amplifier 34. Specifically, a seven-digit signal is supplied over bus 37 to logic receiver 238. Bits 0 through 4 constitute a first selection signal and select a first specified transducer 26 to be connected. The data supplied over bits 0–4 will be referred to as a channel identifier.

Bits 5 and 6 constitute a multiple connection code and serve to indicate the number of additional adjacent transducers 26 whose output will be connected in common with the output of the transducer 26 specified by the channel identifier. That is, the multiple connection code may have values of 0, 1, 2, or 3 to specify that zero, one, two, or three transducers adjacent to the first specified transducer are to have their outputs combined with the output of the first specified transducer.

The channel identifier is supplied over bus 82 to bus 82B connected to address input terminals 88A of PROM 84A and also to bus 82A connected in common to address input terminals 70B of multiplexer device 60B and 72B of multiplexer device 62B. In tne preferred embodiment, a maximum of 32 channels are provided. Therefore, the five-bit channel identifier will have a maximum value of 1F in hexidecimal notation and 32 in decimal notation. It should be noted that the channel identifier is a five-bit value. Thus, the high order bit of the channel identifier indicates whether the specified transducer is in the first group of 16 transducers (i.e., 26-1 through 26-16) or the second group of 16 transducers (i.e., 26-17 through 26-32). The high order bit of the channel identifier, unlike the four low order bits, is not supplied to address input terminals of multiplexer devices 60B and 62B. Rather, the high order bit of the channel identifier is supplied to enable terminal 226 of multiplexer device 62B and through invertor 256 to enable terminal 210 of multiplexer device 60B. It can therefore be appreciated that multiplexer devices 60B and 62B are enabled on a mutually exclusive basis according to the logic state of the high-order bit of the channel identifier. That is, when the channel identifier is specifying a transducer in the group 26-1 through 26-16, multiplexer device 60B is enabled and multiplexer device 62B is disabled. However, when the channel identifier is specifying a transducer in the second group 26-17 through 26-32 and thus has a value of 10H through 1FH, the high order bit is a logic 1, thus enabling multiplexer device 62B and disabling multiplexer device 60B.

The low order bits of the channel identifier are supplied to address inputs of multiplexer devices 60B and 62B. Assuming, for example, that the channel identifier is less than 10H, the lower order bits of the channel identifier will be supplied to address input terminal 70B of multiplexer device 60B. Since enable terminal 210 is activated, multiplexer device 60B will cause a signal input terminal 66B specified by the value of the four low order bits of the channel identifier to be connected to output terminal 202. Thus, the output signal of the selected transducer 26 is supplied over output terminal 200 and line 106 to input terminal 104 of analog switch 104. Since enable terminal 210 of logic device 60B is also connected to an input of NOR gate 250, input terminal 116B of analog switch 104 is activated, causing input terminal 114 to be connected to output terminal 117 of switch 104 and through analog buffer 122 to amplifier 34.

Since the multiple connection code is supplied over bus 96 to the high order address input terminals 86A, 86B, and 86C, it can be seen in FIG. 4A that a multiple connection code of 0 will access data set 300. Since data set 300 contains all zeros, the data output terminals 86A will also provide an output of all zeros. Similarly, from FIGS. 4B and 4C, it can be seen that a multiple connection code of 0 will result in access to data sets 310 and 320, respectively, similarly causing data output terminals 86B and 86C to provide an output of all zeros. Thus, no additional multiplexer 60A, 60C, 60D or 62A, 62C, or 62D will be activated.

Assume that a multiple connection code of 1 is specified by microcomputer 24. Thus, in addition to the transducer 26 specified by the channel identifier, a further transducer 26 will be connected in common with the transducer specified by the channel identifier in the following manner. A multiple connection code of 1 will access data set 302 (FIG. 4A) of PROM 84A. Thus, a non zero value will be supplied at data output terminals 86A of PROM 84A. Assume that a channel identifier of 0 was simultaneously supplied by microcomputer 24 with a multiple connection code of 1. A channel identifier of 0 will cause multiplexer 60B to establish a connection between signal input terminal 66B-1 and output terminal 202. However, the combination of channel identifier of 0 and a multiple connection code of 1 will produce an input to address inputs 88A of PROM 84A having a value of 20H. Thus, as can be seen from FIG. 4A, a data value from data set 302 of 11H will be supplied at data output terminals 86A of PROM 84A. This will cause enable terminal 214 of multiplexer device 60D to become activated and place a value of 1H at address input terminal 70D of multiplexer 60D. Accordingly, signal input 66D-2 of multiplexer device 60D will be connected to output terminal 206 and will thus be connected in common over line 106 with the output of transducer 26-1.

A multiple connection code of 1 generated simultaneously with a channel identifier of 0 will cause an address of 20H to be applied to address terminals 88B and 88C of PROMs 84B and 84C, respectively. As can be seen from FIGS. 4B and 4C, data sets 312 and 322 will be accessed, resulting in an output of 0 from data output terminals 86B, 86C of PROMs 84B and 84C, respectively. Thus, no additional transducers, other than those specified in the preceding paragraph, are connected in common.

When computer 24 generates a multiple connection code of 2, an address value between 40H and 5FH will be supplied to address input terminals 88A, 88B, 88C of PROMs 84A, 84B and 84C, respectively. Data from data sets 304, 314, and 324 will thus be accessed, the specific values from such data sets being dependent upon the channel identifier also supplied simultaneously by microcomputer 24. For example, if a channel identifier of 0 is supplied simultaneously with a multiple connection code of 2, an address value of 40H is supplied to address input terminals 88A, 88B, 88C of PROMs 84A, 84B and 84C, respectively. In output of 11H is therefore provided from data set 304 in PROM 84A to data output terminals 86A. This will cause enable terminal 214 to become activated, thus providing the output of transducer 26-2 to become connected, through signal input 66D-2 and output terminal 206 of multiplexer device 60D to line 106 in common with the output of transducer 26-2 connected through signal input terminal 66B-1 and output terminal 202 of multiplexer device 60B to line 106. An address input value of 40H (caused by multiple connection code of 2 and a channel identifier of (0) supplied to address input terminals 88B of PROM 84B will cause a value of 12H from data set 314 to be supplied at data output terminals 86B of PROM 84B. This will energize enable output 212 of multiplexer device 60C and a value of 2 to be supplied at address input terminal 70C of multiplexer device 60C. Thus, signal input terminals 66C-3 will be connected to output terminal 204, establishing a common connection of an additional transducer 26-3 to transducer 26-1 and 26-2 over line 106. A hex value of 40 supplied to address input terminals 88C of PROM 84C will access data set 324 as shown in FIG. 4C and will result in a 0 valued output at data output terminals 86C of PROM 84B.

A multiple connection code of 3 supplied by microcomputer 24 simultaneously with a channel identifier of 0 will cause a value of 60 hex to be supplied at address input terminals 88A, 88B, 88c of PROMs 84A, 84B and 84C, respectively. This will access data contained in data sets 306, 316 and 326, respectively as shown in FIGS. 4A, 4B and 4C. Thus, PROM 84A will generate a value of 11H at data output terminals 86A, PROM 84B will generate a value of 12H at data output terminals 86B, and PROM 84C will generate a value of 13H at data output terminals 86C. This will cause the simultaneous connection of four transducers; that is, transducers 26-1, 26-2, 26-3 and 26-4.

The channel identifier of 0 results in multiplexer device 60B connecting the output of transducer 26-1 through signal input terminals 66B-1 and output terminal 202 to line 106. PROM 84A generates a value of 11H at data output terminals 86A, causing multiplexer device 60D to connect the output of transducer 26-2 through signal input 66D-2 and output terminal 206 to line 106. A data output value of 12H generated at output terminals 86B of PROM 84B will cause multiplexer 60C to connect the output of transducer 26-3 through signal input terminal 66C-3 and output terminal 204 to line 106. Finally, a data output value of 13H at data output terminals 86C of PROM 84C will cause energization of enable terminal 208 of multiplexer 60A, and establish connection of transducer 26-4 through signal input terminal 66A-4 and output terminal 200 to line 106.

For each of the aforementioned examples, enable terminals 224, 226, 228, and 230 of multiplexer devices 62A, 62B, 62C and 62D remain deenergized, thus insuring that no transducers 26-17 through 26-32 will be connected. Moreover, inputs to NOR gates 248 and 250 insure that only control terminal 116B of analog switch 104 is energized, thereby providing connection of only line 106 to ouput terminal 114 of analog switch 104. A channel identifier code of 10H through 1FH will result in enable terminals 208, 210, 212 and 214 being deenergized and at least one of enable terminals 224, 226, 228 and 230 of multiplexer devices 62A, 62B, 62C and 62D, respectively being activated. Since the aforementioned enable terminals are also connected to inputs of NOR gates 248 and 250, such energization and deenergization of enable terminals will result in deenergization of control terminal 116B and energization of control terminal 116A of analog switch 104. Multiplexer device 62B will thus be energized for channel identifiers between 10 and 1FH (16 and 32 decimal). In addition, multiple connection codes of 1, 2, or 3 will result in energization of multiplexer devices 62D, 62D and 62C, and 62D and 62C and 62A, respectively.

When a combination of channel identifier and multiple connection code results in simultaneous energization of at least one transducer of the group 26-1 through 26-16 and another transducer of the group 26-17 through 26-32, at least one multiplexer device of circuit 60 and one multiplexer device of circuit 62 will be simultaneously enabled, causing simultaneous activation of both control terminals 116A and 116B of analog switch 104. For example, a channel identifier code of F and a multiple connection code of 1 will operate to cause simultaneous common connection between the outputs of transducer 26-16 and 26-17. That is, a channel identifier of F (15 decimal) will be transmitted over bus 82 and 82A to input terminal 70B of multiplexer device 60B. In addition, the combination of a channel identifier of F and a multiple connection code of 1 will result in a value of 2F being applied to address input terminals 88A, 88B and 88C of PROMs 84A, 84B, and 84C, respectively. This address input value will access data set 302 of PROM 84A and cause a value of 20H to be generated at data ouput terminals 86A of PROM 84A. This will cause enable terminal 230 of multiplexer device 62D to become activated, thus allowing the value of 0 supplied to address terminal 72D of multiplexer device 62D to cause signal input 68D-1 of multiplexer device 62D to be connected to output 222 and thence to line 110. Enable terminal 230 is connected to NOR gate 248 and enable terminal 210 is connected to NOR gate 250. Thus, energization of enable terminals 230 and 210 will cause simultaneous energization of control terminals 116A and 116B of analog switch 104, permitting simultaneous common connection of transducer 26-16 and 26-17 at output terminal 114.

It can thus be seen that memory device 84 includes PROMs 84A, 84B, and 84C which include data sets 300, 302, 304, 306, 310, 312, 314, 316, 320, 322, 324 and 326. Data sets 300, 302, 304, and 306 correspond to multiplexer devices 60D and 62D for multiple connection codes of 0, 1, 2, and 3, respectively. Data sets 310, 312, 314 and 316 correspond to multiplexer devices 60C and 62C for multiple connection codes of 0, 1, 2, and 3, respectively. Data sets 320, 322, 324, and 326 correspond to multiplexer devices 60A and 62A for multiple connection codes 0, 1, 2, and 3, respectively.

In the preferred embodiment, a maximum of thirty two transducers are supplied to connection circuit 30 and a maximum of 4 transducers 26 may be connected in common at any one time. However, the invention is not so limited. Additional multiplexer devices identical to devices 60A-D and 62A-D could be connected according to the principles described above in a manner to provide multiple connection of any number of transducers and any number of simultaneous connections.

Referring now to FIG. 5, high voltage pulser circuit 16 is shown greater detail. High voltage pulser circuit 16 contains 32 identical channel pulser circuits 300. Each channel pulser circuit 300 includes an amplifier 302 connected to the output of one line of bus 18. The output of amplifier 302 is fed through inverting amplifier 304 to the control terminal of a high voltage switching transistor 306. High voltage switching transistor 306 is connected in series between a transmitting transducer 12 and a high voltage power supply 308. In the preferred embodiment, high voltage switching transistor 306 comprises a type RF 330 transistor commercially available from the International Rectifier Corporation of L. El Segundo, Calif. Further, in the preferred embodiment, high voltage power supply 308 supplies approximately 600 volts to transistor 306 of each circuit 300.

Referring now to FIG. 6, pulser/receiver control circuit 20 is shown in greater detail. Bus 22 from microcomputer 24 is connected to a bus transceiver 320 and an address decoder circuit 322. The output of transceiver 320 is connected in parallel to input/output port expanders 324, 326, and 328, each of which comprises output ports A, B, and C. In the preferred embodiment, bus transceiver 320 comprises a type 8287 bus tranceiver. Expanders 324, 326, and 328 each comprise a type 8255-5 integrated circuit. Both of the aforementioned types of integrated circuits are commercially obtainable from the Intel Corporation. Address decoder circuit 322 in the preferred embodiment comprises a type 74S138 octal decoder integrated circuit commercially available from Texas Instruments Incorporated of Dallas, Tex.

Control lines from bus 22 are connected to timing circuitry 330 which in turn controls transceiver 320 and generates appropriate control signals back to microcomputer 24. Additional control lines 332 are connected from bus 22 to control terminals of expanders 324, 326, and 328. Timing and control circuits 330 and 332 are operated in accordance with the Intel Multibus protocol.

The invention includes pulse means for simultaneously generating an energizing pulse to transmitting transducers 12 in selected groups. As shown in FIG. 6, separate groups of eight data output lines from ports A and B of expanders 324 and 326 are connected through a pairs of latch circuits 334 and 336 to enable terminals of four-channel switching circuits 338. Circuits 338 may be type 74LS126 integrated circuit commercially available from Texas Instruments, Inc. The control terminals of switching circuits 338 are connnected to a pulse width circuit 340 controlled by a line 342 from port C of expander 324 and are responsive to a pulse command signal generated by pulse width circuit 340 from the signal on line 342 and from input 19 by which an operator has entered a desired pulse width value.

An analog-to-digital converter (ADC) 350 is connected to port C of expander 326. The input to ADC 350 is connected to the analog output line 35 from amplifier 34 of FIG. 1. Gate signal 38A from gate circuit 36 of FIG. 1 is connected through a delay circuit 352 to the START CONVERSION terminals 354 of ADC 350. ADC 350 also includes an END-OF-CONVERSION terminal connected over a line 356 to port C of expander 326.

Port A of expander 328 provides seven output lines connected through bus 37 to connection circuits 30 and 32 of FIG. 1.

The operation of FIGS. 5 and 6 will now be described. Computer 24 generates control signals to energize one or more transducers 12 by supplying eight-bit bit patterns to ports A and B of expanders 324 and 326. There thus is a one-for-one correspondence between transducers 12, output lines of expanders 324 and 326, and the bits of bit patterns supplied to expanders 324 and 326. The bit patterns are latched in latches 334 and 336 to enable appropriate switches in four-channel switching circuits 338. Thus, a bit pattern of 04H sent to port A of expander 324 will enable transducer 12-3, a bit pattern of 80H sent to port B of expander 324 will enable transducer 12-16, a bit pattern of 0C0H sent to port A of expander 326 will enable transducers 12-23 and 12-24, a bit pattern of 0FH to port A of expander 324 will enable transducers 12-1, 12-2, 12-3, and 12-4, and so on. However, circuits 338 are not yet activated.

Computer 24 then transmits the bit pattern over bus 22 through transceiver 320, expander 328, and bus 37 to connection circuit 30 to set up the proper grouping of receiving transducers 26. Computer 24 then generates a pulse command through port C of expander 324 and line 342 to pulse width circuit 340. Pulse width circuit 340 generates a pulse of appropriate width which is supplied to switching circuits 338 to activate the enabled switches in circuits 338 to supply a pulse of the specified width to corresponding circuits 300 of pulser circuit 16.

Figure 7A:
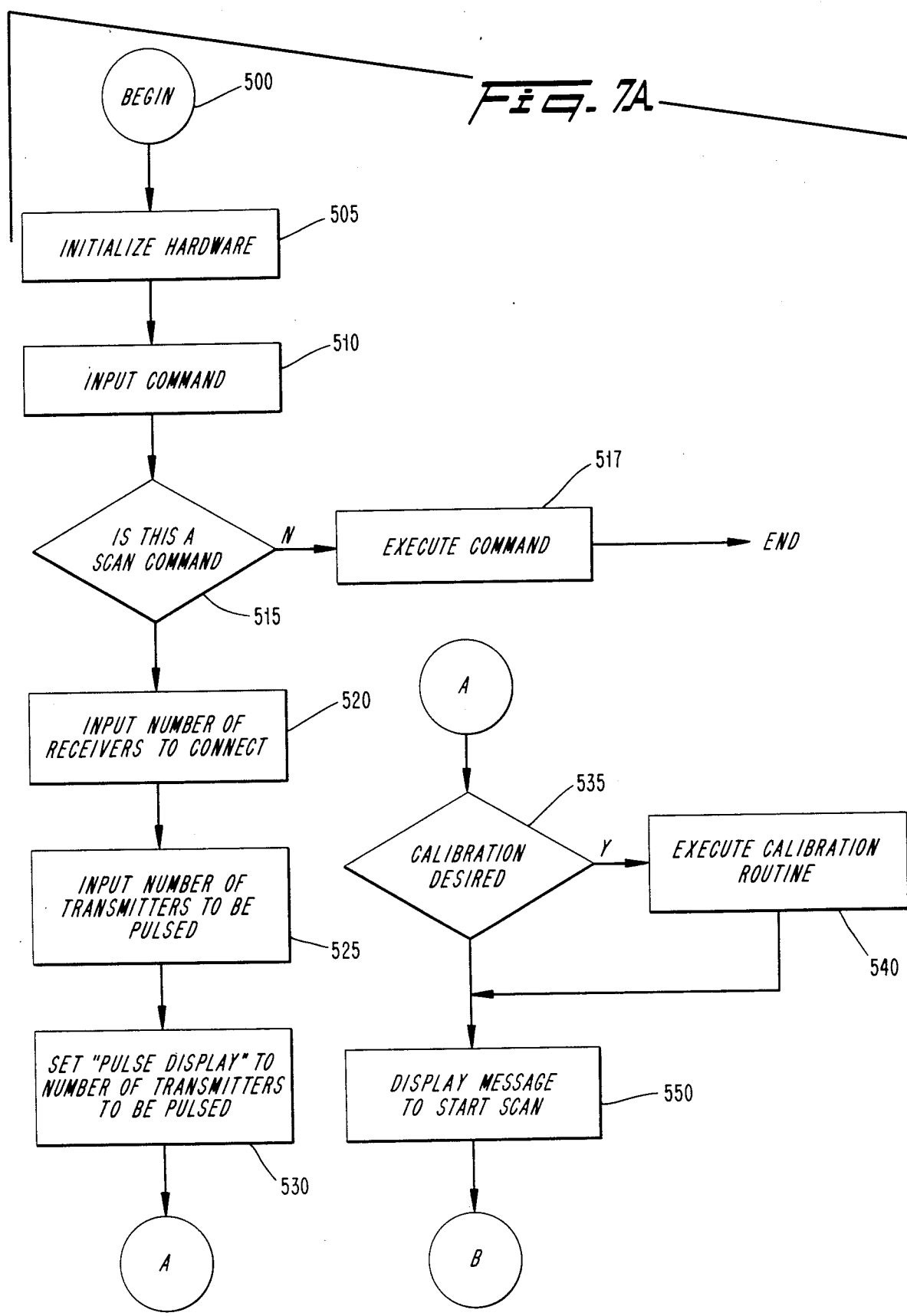
FIGS. 7A and 7B are logic flow diagrams of a control program executed by microcomputer 24.

Referring now to FIG. 7A, there is shown a logic flow diagram of instructions stored in memory of microcomputer 24 to perform ultrasonic inspection of workpiece 28. As can be seen in FIG. 7A, execution of the program begins at block 500 by executing a call to the operating system of microcomputer 24 to initiate the ultrasonic inspection program. This call is entered over computer terminal 48. At block 505, various hardware initialization steps are performed, including the allocation of proper memory in microcomputer 24, set up of printer 46, initialization of video display 44, initialization of input/output ports on microcomputer 24, and various other miscellaneous initialization procedures. Next, at block 510, a request is made at computer terminal 48 for the operator to enter a command. Permissible commands include initiate ultrasonic inspection scanning, initiate a video test sequence, and various other adjustment and debugging procedures.

At block 515, a determination is made if a scanning command has been entered. If not, the appropriate command is executed at block 517 and the program ends.

If a scanning command has been entered, a message is provided at block 520 at computer terminal 48 requesting the operator to enter the number of receivers whose outputs are to be simultaneously connected for each data value. Next, a request is made at block 525 for the operator to enter the number of transmitting transducers 12 to be simultaneously energized with each scanning pulse. At block 530, this number is stored in a variable entitled PULSE DISPLAY for use by software in microcomputer 24 to generate the proper scanning pulses.

At block 535, a determination is made if a calibration routine has been requested by the operator at block 510. If so, the calibration routine is executed at block 540. If calibration has not been requested, program control advances to block 550 where a message is displayed to cause the operator to initiate operation of scanning bridge 53.

Figure 7B:
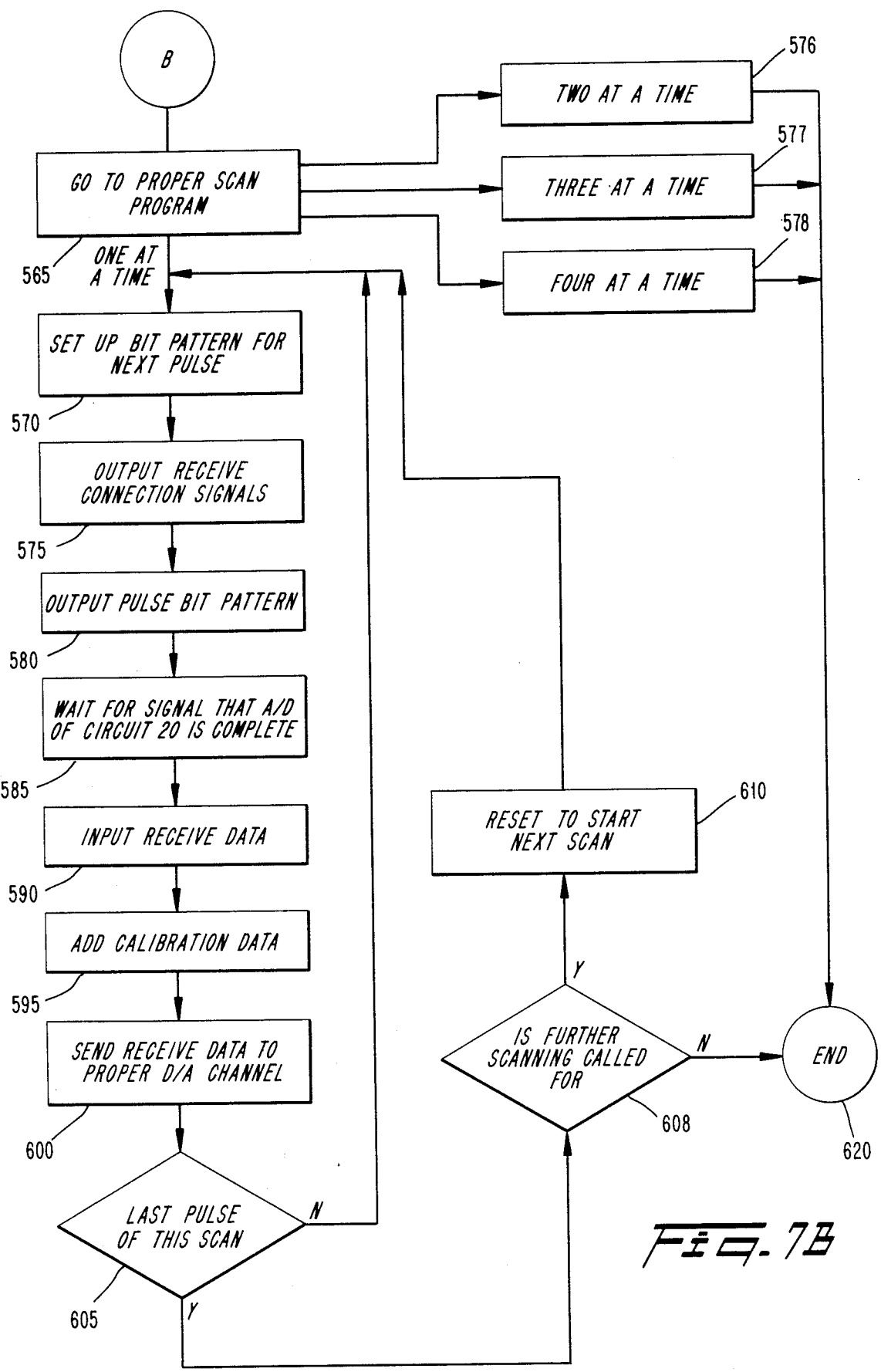

Referring now to FIG. 7B, the proper scan routine is entered at block 565 according to the number of transmitting transducers 12 which are desired to be energized for each inspection pulse. The scan program for single element pulsing is shown in FIG. 7B.

The bit pattern for the next transducer scanning pulse is then set up at block 570. Next, at block 575 the channel identifier for the next receiving transducer 26 is ORed with the multiple connection code generated from the information received at block 520 and a bit pattern outputted to circuit 20 to establish common connection of one or more receiving transducers 26. At block 580 the pulse bit pattern set up at block 570 is outputted to pulser circuit 16. Next, a delay loop is entered at block 585 until receipt of a signal from circuit 20 indicating that an analog to digital conversion of received data has taken place.

At block 590, data from the selected received transducer 26 is receive from circuit 20 over an input port of microcomputer 24. Calbration correction data is then added to the received data at 595 and the corrected data supplied at block 600 to an associated channel of DAC 50. A determination is made at block 605 if this is the last channel of the scan. If not, the program returns to block 570 to generate the next inspection pulse of this scan of array 12. If so, a new scan is initiated at block 610 before returning to block 570. The process continues until interrupted by an input from terminal 48.

The invention includes calibration means for correcting data output signals from receiving transducers 26 to compensate for individual variation in response of transducers 26. The calibration means includes means for calculating and storing difference values for each transducer 26, the difference values representing the difference between data output signals for each transducer 26 and the largest of the data output signals. Referring now to FIG. 8, there is shown a logic flow diagram of the calibration routine executed by microcomputer 24. At block 700, transmitting transducers 12 are pulsed in groups as specified by operator entered commands and receiving transducers 26 have their outputs combined in groups as also specified by operator entered commands. Pulsing and receiving of the selected groups is repeated for fifty times to stabilize the electronics and hardware. At block 705, all storage arrays used for calibration purposes are initialized to 0. A calibration flag is set at block 707.

At block 710, the selected transmitting transducer and receiving transducer groups are pulsed and received for two hundred fifty times, and the received values from the selected received transducer groups are averaged. The average value for each group is stored at block 715 and a difference value calculated at block 720 between the highest average value for any group and the average value for each group. The difference for each group is then stored in a calibration difference array. The routine exits at block 725.

As was previously described with regard to block 595 of FIG. 7B, the calibration difference data is added during each scan subsequent to the calibration routine to the received data for each group. In this manner, variations in the received data which are supplied as output from microcomputer 24 reflect only differences in attenuation between transmitting transducers 12 and receiving transducers 26, and not differences in the response of individual transducers.

It will be apparent to those skilled in the art that modifications and variations can be made in the ultrasonic inspection apparatus and methods of this invention. The invention and its broader aspects is not limited to the specific details, representative methods and apparatus, an illustrative example shown and described. Departure may be made from such details without departing from the spirit or the scope of the general inventive concept.

What is claimed is:

1. An ultrasonic inspection system, comprising:
a plurality of ultrasonic transmitting transducers;
means for simultaneously energizing individual transducers of selectable groups of said transmitting transducers;
a plurality of ultrasonic receiving transducers, each of said receiving transducers generating a data output signal representative of ultrasonic energy received by said receiving transducer; and means for combining said data output signals of selectable groups of said receiving transducers independent of said transmitting transducer groups and for supplying a second output signal representive of said combined data output signals.

2. A system as recited in claim 1 wherein said means for simultaneously energizing individual transducers of selectable groups of said transmitting transducers includes means for energizing groups of adjacent transmitting transducers.

3. A system as recited in claim 2 wherein said means for combining said data output signals of selectable groups of said receiving transducers includes means for combining said data output signals of groups of adjacent receiving transducers.

4. A system as recited in claim 3 wherein said means for simultaneously energizing individual transducers of selectable groups of said transmitting transducers comprises;
   a computer generating a pulse command signal and a bit pattern representative of said groups of transmitting transducers; and
   pulse means for simultaneously generating an energizing pulse to transmitting transducers in said selected groups, said pulse means comprising a control terminal responsive to said pulse command signal and an enable terminal responsive to said bit pattern.

5. A system as recited in claim 4 wherein said means for combining said data output signals of selected groups of said receiving transducers comprises a plurality of multiplexers coupled to said computer.

6. A system as recited in claim 1 further comprising calibration means for adjustably correcting said data output signals from said receiving transducers to compensate for individual variation in the response of said receiving transducers.

7. A system as recited in claim 6 wherein said calibration means comprises means for calculating and storing difference values for each of said receiving transducers, said difference values representing the difference between data output signals for each of said receiving transducers and the largest of said data output signals, and for combining the data output signal of each of said receiving transducers with the corresponding difference value to obtain a compensated data output signal.

8. An ultrasonic inspection system, comprising:
   a plurality of ultrasonic transmitting transducers;
   means for energizing said transmitting transducers;
   a plurality of ultrasonic receiving transducers, each of said receiving transducers generating a data output signal representative of ultrasonic energy received by said receiving transducer; and
   calibration means for correcting said data output signals from said receiving transducers to adjustably compensate said data output signals for individual variations in the response of said receiving transducers.

9. A system as recited in claim 8 wherein said calibration means comprises means for calculating and storing difference values for each of said receiving transducers representative of the difference between data output signals for each of said receiving transducers and the largest of said data output signals, and for combining the data output signal of each of said receiving transducers with the corresponding difference value to obtain a compensated data output signal.

10. A method for generating ultrasonic inspection data representative of a workpiece from an array of ultrasonic transmitting transducers and and an array of ultrasonic receiving transducers which generate data output signals representative of received ultrasonic energy, comprising the steps of:
   energizing the array of ultrasonic transmitting transducers by generating sequential inspection pulses each consisting of ultrasonic energy applied to the workpiece by simultaneously energized transducers of selectable groups of said transmitting transducers; and
   generating sequential output data values by combining the data output signals produced from said ultrasonic energy by groups of said receiving transducers selected independently of the transmitting transducer groups.

11. A method as recited in claim 10 wherein the step of energizing the array of ultrasonic transmitting transducers comprises the steps of:
   sending a binary bit pattern representative of selected transducers to enable channels of a switching device corresponding to the selected transmitting transducers; and
   sending a pulse command signal to said switching device to generate an energizing pulse to said selected transducers.

12. A method as recited in claim 10 wherein the step of combining the data output signals comprises the steps of sending a data selection signal and a multiple connection code to a multiplexer device coupled to the outputs of the selected receiving transducers to couple the data output signals of one of said receiving transducers and the data output signals of a number of adjacent receiving transducers specified by said multiple connection code.

13. A method for compensating the output signals generated by a plurality of ultrasonic receiving transducers in response to ultrasonic inspection signals generated by ultrasonic transmitting transducers, comprising the steps of:
   generating calibration signals consisting of ultrasonic inspection signals from the ultrasonic transmitting transducers;
   generating data output signals from each of said ultrasonic receiving transducers in response to the calibration signals;
   calculating and storing a difference value for each of the ultrasonic receiving transducers equal to the difference between the data output signal generated by each transducer in response to the calibration signals and the largest data output signal generated in response to the calibration signals;
   applying ultrasonic inspection signals from the transmitting transducers to a workpiece;
   generating data output signals from each of the ultrasonic receiving transducers in response to the ultrasonic inspection signals received through the workpiece; and
   adding the difference value for each receiving transducer to the data output signal for the respective ultrasonic receiving transducer to produce a compensated data output signal representative of attenuation by the workpiece.

14. A method as recited in claim 13 wherein the step of calculating and storing difference values comprises the steps of:

repeatedly executing the steps of generating calibration signals and generating data output signals; and calculating and storing the average of the data output signals for each of the ultrasonic receiving transducers.

15. A method as recited in claim 13 wherein the step of generating ultrasonic inspection signals comprises simultaneous energization of data selectable groups of said ultrasonic transmitting transducers;

the step of generating data output signals comprises combining data output signals of second selectable groups of said ultrasonic receiving transducers;

the step of generating calibration signals comprises simultaneous energization of said data selectable groups of said ultrasonic transmitting transducers;

the step of generating data output signals comprises generating calibration output signals from each of said second groups of ultrasonic receiving transducers;

the step of calculating and storing a difference value comprises calculating and storing a difference value for each of said second selectable groups of ultrasonic receiving transducers equal to the difference between the data output signal generated by each of said second selectable groups and the largest data output signal;

the step of adding the difference value comprises adding the difference value for each of said second selectable groups to the data output signal for the respective member of the second selectable group to produce a compensated data output signal.

* * * * *